US005506358A

United States Patent [19]

Takase et al.

[11] Patent Number: 5,506,358
[45] Date of Patent: Apr. 9, 1996

[54] PROCESS FOR PRODUCING ALKOXYIMINOACETAMIDE COMPOUNDS

[75] Inventors: Akira Takase, Otsu; Hiroyuki Kai, Yamatokoriyama; Moriyasu Masui, Yokkaichi; Kazuo Ueda, Suzuka; Tsuneo Iwakawa, Kusatsu, all of Japan

[73] Assignee: Shionogi & Co., Ltd., Osaka, Japan

[21] Appl. No.: 207,055

[22] Filed: Mar. 8, 1994

[30] Foreign Application Priority Data

Mar. 16, 1993 [JP] Japan .................................. 5-056143
Feb. 16, 1994 [JP] Japan .................................. 69-019381

[51] Int. Cl.⁶ ...................... C07D 239/02; C07C 249/04
[52] U.S. Cl. .......................... 544/316; 546/152; 564/147; 562/859; 562/861; 562/862; 562/863
[58] Field of Search ........................... 544/316; 546/152; 564/147; 562/859, 861, 862, 863

[56] References Cited

U.S. PATENT DOCUMENTS 5,112,860  5/1992  Wingert et al. .......................... 514/513

5,185,342  2/1993  Hagase et al. ..
5,187,170  2/1993  Wingert et al. .......................... 514/351

FOREIGN PATENT DOCUMENTS 2049162  3/1992  Canada .
0386940  9/1990  European Pat. Off. .
0432503  6/1991  European Pat. Off. .
0477631  4/1992  European Pat. Off. .

OTHER PUBLICATIONS

March, "Adv. Org. Chem." 2nd Ed. (1977) McGraw-Hill Book Co. pp. 382–383, 398–399.
Chemical Abstracts, vol. 86, No. 15, 1977, Columbus, Ohio US; Abstract No. 106608v, & JP-A-51 091 284 (Fujisawa Pharmaceutical Co., Ltd.) 10 Aug. 1976.

*Primary Examiner*—Johann Richter
*Assistant Examiner*—John Peabody
*Attorney, Agent, or Firm*—Wenderoth, Lind & Ponack

[57] ABSTRACT

There is disclosed a process for producing an alkoxyiminoacetamide compound which is useful as agricultural fungicides. Also dislclosed are novel intermediate compounds for the above process and their production.

20 Claims, No Drawings

PROCESS FOR PRODUCING ALKOXYIMINOACETAMIDE COMPOUNDS

FIELD OF THE INVENTION

The present invention relates to the production of alkoxyiminoacetamide compounds, particularly to an industrial process for producing alkoxyiminoacetamide compounds useful as agricultural fungicides, novel intermediate compounds for the process and their production.

BACKGROUND OF THE INVENTION

Hitherto, the present inventors have studied to develop agricultural fungicides for a long term of years. As a result, it has been found that alkoxyiminoacetamide compounds of the formula (I):

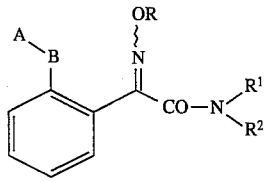

wherein A is hydrogen, lower alkyl, lower alkenyl, lower alkynyl, lower alkoxy, cyclo(lower)alkyl, cyclo(lower)alkenyl, optionally substituted phenyl or an optionally substituted heterocyclic group; B is —$CH_2$—, —O—, —S—, —CH(OH)—, —CO—, —$NR^3$— (wherein $R^3$ is hydrogen or lower alkyl), —$CH_2CH_2$—, —CH=CH—, —C≡C—, —$CH_2O$—, —$CH_2S$—, —$CH_2S(O)$—, —$OCH_2$—, —$SCH_2$—, —$S(O)CH_2$— or epoxy; R is lower alkyl; $R^1$ and $R^2$ are each independently hydrogen or lower alkyl; and the bond ~ represents any configuration of the E-isomer, Z-isomer or a mixture of the E- and Z-isomers; exhibit potent controlling activity against wide varieties of pathogens of plants and cause little damage to useful plants such as grains, vegetables, fruits and the like (see U.S. Pat. No. 5185342 and JP-A 4-182461). The characteristic of the chemical structure of the alkoxyiminoacetamide compound (I) is that the carboxyl group of the acetic acid moiety at the o-position of the benzene ring is converted into an optionally substituted carbamoyl group and that an alkoxyimino group is introduced to the α-position. Based on these characteristics, the compound (I) generally exhibits more excellent fungicidal activity than that of a corresponding alkyl alkoxyiminoacetate wherein the carboxyl group of the carboxylic acid moiety is converted into an alkoxycarbonyl group. The alkoxyiminoacetamide compound (I) exists as the E- or Z-isomer. In general, the E-isomer has superior fungicidal activity to that of the Z-isomer.

OBJECTS OF THE INVENTION

The main object of the present invention is to provide an industrially useful process for producing alkoxyiminoacetamide compounds, particularly a process for producing E-isomers of alkoxyiminoacetamide compounds in high purity.

Another object of the present invention is to provide novel intermediate compounds for the above process.

These objects as well as other objects and advantages of the present invention will become apparent to those skilled in the art from the following description.

SUMMARY OF THE INVENTION

As described above, the present inventors have found that the alkoxyiminoacetamide compounds of the formula (I), particularly their E-isomers, have high utility as agricultural fungicides. Based on this finding, they have studied an industrial process for producing the compounds. As a result, the present invention has been completed.

That is, the present invention provides:

(1) A process for producing an alkoxyiminoacetamide compound of the formula (I):

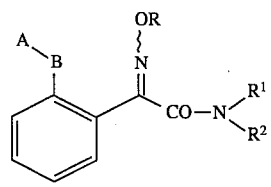

wherein A is hydrogen, lower alkyl, lower alkenyl, lower alkynyl, lower alkoxy, cyclo(lower)alkyl, cyclo(lower)alkenyl, optionally substituted phenyl or an optionally substituted heterocyclic group; B is —$CH_2$—, —O—, —S—, —CH(OH)—, —CO—, —$NR^3$— (wherein $R^3$ is hydrogen or lower alkyl), —$CH_2CH_2$—, —CH=CH—, —C≡C—, —$CH_2O$—, —$CH_2S$—, —$CH_2S(O)$—, —$OCH_2$—, —$SCH_2$—, —$S(O)CH_2$— or epoxy; R is lower alkyl; $R^1$ and $R^2$ are each independently hydrogen or lower alkyl; and the bond ~ represents any configuration of the E-isomer, Z-isomer or a mixture of the E- and Z-isomers; which comprises halogenating a compound of the formula (III):

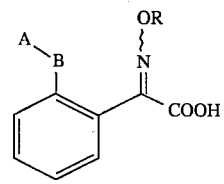

wherein each symbol is as defined above, to obtain a compound of the formula (IV):

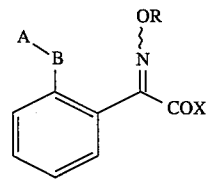

wherein X is halogen and the other symbols are as defined above;

reacting the compound of the formula (IV) with an amine of the formula: $HNR^2R^2$ wherein $R^1$ and $R^2$ are as defined above; and optionally treating the resulting compound with an acid;

(2) A process for producing an alkoxyiminoacetamide compound of the formula (I):

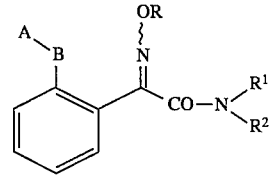

wherein each symbol is as defined in the above (1), which comprises reacting a compound of the formula (IV):

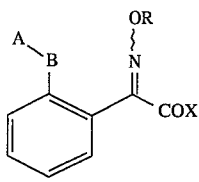

wherein each symbol is as defined in the above (1), with an amine of the formula: HNR¹R² wherein each symbol is as defined in the above (1); and treating the resulting compound with an acid;

(3) A compound of the formula (III):

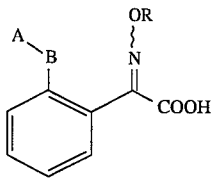

wherein each symbol is as defined for the formula (I);

(4) A process for producing a compound of the formula (III):

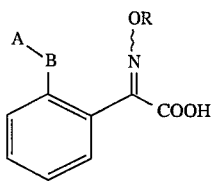

wherein each symbol is as defined for the formula (I), which comprises reacting a compound of the formula (II):

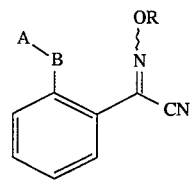

wherein each symbol is as defined for the formula (I), with a base;

(5) A compound of the formula (IV):

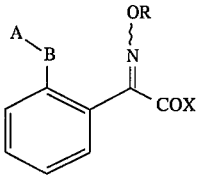

wherein X is halogen and the other symbols are as defined for the formula (I); and (6) A process for producing a compound of the formula (IV):

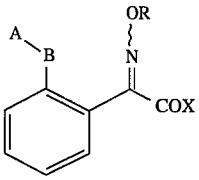

wherein each symbol is as defined in the above (5), which comprises halogenating a compound of the formula (III):

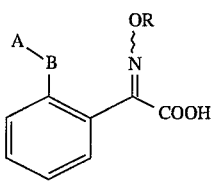

wherein each symbol is as defined for the formula (I).

DETAILED DESCRIPTION OF THE INVENTION

By the term "lower" used in the definitions of the formulas is meant having not more than 8 carbon atoms, preferably not more than 6 carbon atoms, more preferably not more than 4 carbon atoms unless otherwise indicated.

Examples of the lower alkyl represented by R, $R^1$, $R^2$, $R^3$ and A include alkyl having 1 to 6 carbon atoms, preferably 1 to 4 carbon atoms, for example, methyl, ethyl, propyl, isopropyl, butyl, isobutyl, t-butyl and the like.

Examples of the lower alkenyl represented by A include alkenyl having 2 to 8 carbon atoms, preferably 3 to 6 carbon atoms, for example, allyl, propenyl, isopropenyl, butenyl, isobutenyl, pentenyl, hexenyl, hexadienyl and the like.

Examples of the lower alkynyl represented by A include alkynyl having 2 to 6 carbon atoms, preferably 2 to 4 carbon atoms, for example, propargyl, ethynyl, butynyl and the like.

Examples of the lower alkoxy represented by A include alkoxy having 1 to 6 carbon atoms, preferably 1 to 4 carbon atoms, for example, methoxy, ethoxy, propoxy, isopropoxy, butoxy, isobutoxy, s-butoxy, t-butoxy and the like.

Examples of the cyclo(lower)alkyl represented by A include cycloalkyl having 3 to 8 carbon atoms, preferably 3 to 6 carbon atoms, for example, cyclopropyl, cyclopentyl, cyclohexyl and the like.

Examples of the cyclo(lower)alkenyl represented by A include cycloalkenyl having 3 to 8 carbon atoms, preferably 5 to 7 cycloalkenyl, for example, cyclopentenyl, cyclohexenyl and the like.

The optionally substituted phenyl represented by A include unsubstituted phenyl and substituted phenyl.

The optionally substituted heterocyclic group 10 represented by A include unsubstituted heterocyclic groups and substituted heterocyclic groups. The unsubstituted heterocyclic groups are, for example, 5 to 6 membered heterocyclic groups containing in the ring 1 to 3 heteroatoms selected from oxygen, sulfur and nitrogen, which may form condensed ring systems with carbocyclic rings or other heterocyclic rings. Examples of the unsubstituted heterocyclic group include pyridyl, pyrimidinyl, pyridazinyl, pyrazinyl, thiazolyl, benzothiazolyl, benzofuranyl, benzothienyl, oxazolyl, benzoxazolyl, isoxazolyl, pyrazolyl, imidazolyl, quinolyl and the like.

Examples of the substituted phenyl or substituted heterocyclic groups represented by A include phenyl and the above-exemplified heterocyclic groups substituted with a substituent selected from the group consisting of lower alkyl (e.g., methyl, ethyl, propyl, butyl, etc.), lower alkenyl (e.g., vinyl, allyl, crotyl, etc.), lower alkynyl (e.g., ethynyl, propargyl, butynyl, etc.), cycloalkyl (e.g., cyclopropyl, cyclopentyl, cyclohexyl, etc.), cycloalkenyl (e.g., cyclopentenyl, cyclohexenyl, etc.), lower alkanoyl (e.g., acetyl, propionyl, isobutyryl, etc.), lower alkylsilyl (e.g., methylsilyl, ethylsilyl, propylsilyl, butylsilyl, etc.), halogenated lower alkyl (e.g., trifluoromethyl, chloromethyl, 2-bromoethyl, 1,2-dichloropropyl, etc.), di(lower)alkylamino (e.g., dimethylamino, diethylamino, etc.), phenyl, phenyl(lower)alkyl (e.g., benzyl, phenethyl, etc.), phenyl(lower)alkenyl (e.g., styryl, cinnamyl, etc.), furyl(lower)alkyl (e.g., 3-furylmethyl, 2-furylethyl, etc.), furyl(lower)alkenyl (e.g., 3-furylvinyl, 2-furylallyl, etc.), halogen (e.g., fluorine, chlorine, bromine, iodine), nitro, cyano, —$OR^4$ [wherein $R^4$ is hydrogen, lower alkyl (e.g., methyl, ethyl, propyl, etc.), lower alkenyl (e.g., vinyl, allyl, crotyl, etc.), lower alkynyl (e.g., ethynyl, 2-propynyl, 3-butynyl, etc.), lower alkanoyl (e.g., acetyl, propionyl, butyryl, etc.), phenyl, lower alkoxyphenyl (e.g., 3-methoxyphenyl, 4-ethoxyphenyl, etc.), nitrophenyl (e.g., 3-nitrophenyl, 4-nitrophenyl, etc.), phenyl(lower)alkyl (e.g., benzyl, phenethyl, phenylpropyl, etc.), cyanophenyl (lower)alkyl (e.g., 3-cyanophenylmethyl, 4-cyanophenylethyl, etc.), benzoyl, tetrahydropyranyl, pyridyl, trifluoromethylpyridyl, pyrimidinyl, benzothiazolyl, quinolyl, benzoyl(lower)alkyl (e.g., benzoylmethyl, benzoylethyl, etc.), benzenesulfonyl or lower alkylbenzenesulfonyl (e.g., toluenesulfonyl, etc.)] and —$CH_2$—Z—$R^5$ [wherein Z is —O—, —S— or —$NR^6$— (wherein $R^6$ is hydrogen or lower alkyl), $R^5$ is phenyl, halophenyl (e.g., 2-chlorophenyl, 4-fluorophenyl, etc.), lower alkoxyphenyl (e.g., 2-methoxyphenyl, 4-ethoxyphenyl, etc.), pyridyl or pyrimidinyl].

These substituents of the phenyl or heterocyclic group represented by A may be at any possible position on the ring and may be the same or different. The number of the substituents is 1 to 5, preferably 1 to 4, more preferably 1 to 3.

Examples of the halogen represented by X include fluorine, chlorine, bromine and iodine.

In the processes of the present invention, A is preferably optionally substituted phenyl such as unsubstituted phenyl or phenyl substituted with lower alkyl and/or halogen; or an optionally substituted heterocyclic group such as unsubstituted pyridyl or pyridyl substituted with halogen and/or halogenated lower alkyl. B is preferably —O—, —$CH_2O$— or —$OCH_2$—.

In the processes of the present invention, A is more preferably phenyl substituted with mono- or dimethyl and/or chlorine or fluorine (e.g., 2-methylphenyl, 2,5-dimethylphenyl, 3,5-dimethylphenyl, 3,4-dimethylphenyl, 4-fluorophenyl, 4-chlorophenyl, 2-methyl-4-chlorophenyl, etc.) or pyridyl optionally substituted with chlorine and/or trifluoromethyl (e.g., pyridyl, 2-chloropyridyl, 3,5-dichloropyridyl, 2-trifluoromethylpyridyl, 3-trifluoromethylpyridyl, 5-trifluoromethylpyridyl, 2-chloro-3-trifluoromethylpyridyl, 2-chloro-5-trifluoromethylpyridyl, 5-chloro-3-trifluoromethylpyridyl, 3-chloro-5-trifluoromethylpyridyl, 6-chloro-3-trifluoromethylpyridyl, etc.). B is more preferably —O— or —$OCH_2$. R is preferably methyl. $R^1$ is preferably hydrogen. $R^2$ is preferably methyl.

The compound (I), (II), (III) and (IV) may be any of its E-isomer, Z-isomer or mixtures of the E- and Z-isomers. This is indicated by the wave line (~) in the formulas. The compound (I) is preferably an E-isomer.

Specific examples of the desired alkoxyiminoacetamide compound (I) are described below (see U.S. Pat. No. 5185342 and JP-A 4-182461). Each of the following compounds includes its (E)-isomer and (Z)-isomer, but the (E)-isomer is preferred.

N-methyl-2-[2-(2,5-dimethylphenoxymethyl)phenyl]-2-methoxyiminoacetamide;
2-(2-phenoxyphenyl)-2-methoxyiminoacetamide;
N,N-dimethyl-2-(2-phenoxyphenyl)-2-methoxyiminoacetamide;
N-methyl-2-(2-phenoxyphenyl)-2-methoxyiminoacetamide;
N-methyl-2-[2-(3-tolyloxy)phenyl]-2-methoxyiminoacetamide;
N-methyl-2-[2-(4-nitrophenoxy)phenyl]-2-methoxyiminoacetamide;
N-methyl-2-[2-(2-nitrophenoxy)phenyl]-2-methoxyiminoacetamide;
N-methyl-2-[2-(4-acetylphenoxy)phenyl]-2-methoxyiminoacetamide;
N-methyl-2-[2-(4-chlorophenoxy)phenyl]-2-methoxyiminoacetamide;
N-methyl-2-[2-(4-bromophenoxy)phenyl]-2-methoxyiminoacetamide;
N-methyl-2-[2-(4-t-butylphenoxy)phenyl]-2-methoxyiminoacetamide;
N-methyl-2-[2-(4-methoxyphenoxy)phenyl]-2-methoxyiminoacetamide;
N-methyl-2-[2-(4-trimethylsilylphenoxy)phenyl]-2-methoxyiminoacetamide;
N-methyl-2-[2-(4-iodophenoxy)phenyl]-2-methoxyiminoacetamide;
N-methyl-2-[2-(4-chloro-3-methylphenoxy)phenyl]-2-methoxyiminoacetamide;
N-methyl-2-[2-(2-tolyloxy)phenyl]-2-methoxyiminoacetamide;
N-methyl-2-[2-(4-tolyloxy)phenyl]-2-methoxyiminoacetamide;
N-methyl-2-[2-(2,4-diisopropylphenoxy)phenyl]-2-methoxyiminoacetamide;
N-methyl-2-[2-(4-isopropylphenoxy)phenyl]-2-methoxyiminoacetamide;
N-methyl-2-[2-(3,4-dichlorophenoxy)phenyl]-2-methoxyiminoacetamide;
N-methyl-2-[2-(3-benzyloxyphenoxy)phenyl]-2-methoxyiminoacetamide;
N-methyl-2-[2-(3-methoxyphenoxy)phenyl]-2-methoxyiminoacetamide;
N-methyl-2-[2-(3-phenoxyphenoxy)phenyl]-2-methoxyiminoacetamide;
N-methyl-2-[2-(4-phenoxyphenoxy)phenyl]-2-methoxyiminoacetamide;
N-methyl-2-[2-(2,4-dichloro-5-phenoxyphenoxy)phenyl]-2-methoxyiminoacetamide;
N-methyl-2-(2-benzyloxyphenyl)-2-methoxyiminoacetamide;
N-methyl-2-(2-phenoxymethylphenyl)-2-methoxyiminoacetamide;
N-methyl-2-[2-(3-phenoxyphenoxymethyl)phenyl]-2-methoxyiminoacetamide;
N-methyl-2-[2-(4-bromophenoxymethyl)phenyl]-2-methoxyiminoacetamide;
N-methyl-2-[2-(3-methoxyphenoxymethyl)phenyl]-2-methoxyiminoacetamide;
N-methyl-2-[2-(3-chlorophenoxymethyl)phenyl]-2-methoxyiminoacetamide;
N-methyl-2-[2-(2-chlorophenoxymethyl)phenyl]-2-methoxyiminoacetamide;
N-methyl-2-[2-(4-styrylphenoxymethyl)phenyl]-2-methoxyiminoacetamide;
N-methyl-2-[2-(4-benzoylphenoxymethyl)phenyl]-2-methoxyiminoacetamide;
N-methyl-2-[2-(4-t-butylphenoxymethyl)phenyl]-2-methoxyiminoacetamide;
N-methyl-2-[2-(4-methylphenoxymethyl)phenyl]-2-methoxyiminoacetamide;
N-methyl-2-[2-(4-cyanophenoxymethyl)phenyl]-2-methoxyiminoacetamide;

N-methyl-2-[2-(2,4-dichlorophenoxymethyl)phenyl]-2-methoxyiminoacetamide;
N-methyl-2-[2-(3,4-dichlorophenoxymethyl)phenyl]-2-methoxyiminoacetamide;
N-methyl-2-[2-(3,5-dichlorophenoxymethyl)phenyl]-2-methoxyiminoacetamide;
N-methyl-2-[2-(3-trifluoromethylphenoxymethyl)phenyl]-2-methoxyiminoacetamide;
N-methyl-2-[2-(3-dimethylaminophenoxymethyl)phenyl]-2-methoxyiminoacetamide;
N-methyl-2-[2-(3-bromophenoxymethyl)phenyl]-2-methoxyiminoacetamide;
N-methyl-2-[2-(3-nitrophenoxymethyl)phenyl]-2-methoxyiminoacetamide;
N-methyl-2-[2-(4-fluorophenoxymethyl)phenyl]-2-methoxyiminoacetamide;
N-methyl-2-[2-(3-isopropoxyphenoxymethyl)phenyl]-2-methoxyiminoacetamide;
N-methyl-2-[2-(4-chlorophenoxymethyl)phenyl]-2-methoxyiminoacetamide;
N-methyl-2-(2-phenylthiomethylphenyl)-2-methoxyiminoacetamide;
N-methyl-2-(2-phenylsulfinylmethylphenyl)-2-methoxyiminoacetamide;
N-methyl-2-[2-(3-methyl-2-butenyloxy)phenyl]-2-methoxyiminoacetamide;
N-methyl-2-[2-(3,7-dimethyl-2,6-octadienyloxy)phenyl]-2-methoxyiminoacetamide;
N-methyl-2-[2-(3,3-dichloro-2-propenyloxy)phenyl]-2-methoxyiminoacetamide;
N-methyl-2-[2-(5-trifluoromethylpyridin-2-yloxy)phenyl]-2-methoxyiminoacetamide;
N-methyl-2-[2-(3-trifluoromethylpyridin-2-yloxy)phenyl]-2-methoxyiminoacetamide;
N-methyl-2-[2-(5-trifluoromethylpyridin-2-yloxymethyl)phenyl]-2-methoxyiminoacetamide;
N-methyl-2-[2-(2-pyrimidinyloxymethyl)phenyl]-2-methoxyiminoacetamide;
N-methyl-2-[2-(2-pyridyloxymethyl)phenyl]-2-methoxyiminoacetamide;
N-methyl-2-(2-phenylthiophenyl)-2-methoxyiminoacetamide;
N-methyl-2-[2-(3-hydroxyphenoxy)phenyl]-2-methoxyiminoacetamide;
N-methyl-2-[2-(3-tetrahydropyran-2-yloxyphenoxy)phenyl]-2-methoxyiminoacetamide;
N-methyl-2-[2-(3-pyrimidin-2-yloxyphenoxy)phenyl]-2-methoxyiminoacetamide;
N-methyl-2-{2-[3-(5-trifluoromethylpyridin-2-yloxy)phenoxy]phenyl}-2-methoxyiminoacetamide;
N-methyl-2-{2-[3-(3-methoxyphenoxy)phenoxy]phenyl}-2-methoxyiminoacetamide;
N-methyl-2-{2-[3-(2-nitrophenoxy)phenoxy]phenyl}-2-methoxyiminoacetamide;
N-methyl-2-[2-(3-quinolin-2-yloxyphenoxy)phenyl]-2-methoxyiminoacetamide;
N-methyl-2-[2-(3-benzothiazol-2-yloxyphenoxy)phenyl]-2-methoxyiminoacetamide;
N-methyl-2-[2-(3-benzoylmethyloxyphenoxy)phenyl]-2-methoxyiminoacetamide;
N-methyl-2-[2-(3-toluenesulfonyloxyphenoxy)phenyl]-2-methoxyiminoacetamide;
N-methyl-2-[2-(3-acetyloxyphenoxy)phenyl]-2-methoxyiminoacetamide;
N-methyl-2-[2-(3-benzoyloxyphenoxy)phenyl]-2-methoxyiminoacetamide;
N-methyl-2-{2-[3-(2-cyanobenzyloxy)phenoxy]phenyl}-2-methoxyiminoacetamide;
N-methyl-2-{2-[3-(2-propynyloxy)phenoxy]phenyl}-2-methoxyiminoacetamide;
N-methyl-2-[2-(3-styryloxyphenoxy)phenyl]-2-methoxyiminoacetamide;
N-methyl-2-{2-[3-(2-furan-2-ylvinyl)phenoxy]phenyl}-2-methoxyiminoacetamide;
N-methyl-2-[2-(4-hydroxyphenoxy)phenyl]-2-methoxyiminoacetamide;
N-methyl-2-[2-(4-benzyloxyphenoxy)phenyl]-2-methoxyiminoacetamide;
N-methyl-2-[2-(3-benzyloxyphenoxy)phenyl]-2-methoxyiminoacetamide;
N-methyl-2-[2-(3-phenylthiomethylphenoxy)phenyl]-2-methoxyiminoacetamide;
N-methyl-2-{2-[3-(N-methylanilinomethyl)phenoxy]phenyl}-2-methoxyiminoacetamide;
N-methyl-2-{2-[3-(2-pyridyloxymethyl)phenoxy]phenyl}-2-methoxyiminoacetamide;
N-methyl-2-{2-[3-(phenylsulfinylmethyl)phenoxy]phenyl}-2-methoxyiminoacetamide;
N-methyl-2-{2-[3-(pyrimidin-2-yloxymethyl)phenoxy]phenyl}-2-methoxyiminoacetamide;
N-methyl-2-{2-[3-(4-methoxyphenoxymethyl)phenoxy]phenyl}-2-methoxyiminoacetamide;
N-methyl-2-{2-[3-(4-bromophenoxymethyl)phenoxy]phenyl}-2-methoxyiminoacetamide;
N-methyl-2-[2-(3-phenoxymethylphenoxy)phenyl]-2-methoxyiminoacetamide;
N-methyl-2-(2-(E)-styrylphenyl)-2-methoxyiminoacetamide;
N-methyl-2-(2-(Z)-styrylphenyl)-2-methoxyiminoacetamide;
N-methyl-2-{2'-[(1"S*,2"R*)-1",2"-epoxy-2"-phenylethyl]phenyl}-2-methoxyiminoacetamide;
N-methyl-2-{2'-[(1"R*,2"R*)-1",2"-epoxy-2"-phenylethyl]phenyl}-2-methoxyiminoacetamide;
N-methyl-2-(2-phenylethylphenyl)-2-methoxyiminoacetamide;
N-methyl-2-[2-(α-hydroxybenzyl)phenyl]-2-methoxyiminoacetamide;
N-methyl-2-(2-benzoylphenyl)-2-methoxyiminoacetamide;
N-methyl-2-[2-(2-phenylphenoxymethyl)phenyl]-2-methoxyiminoacetamide;
N-methyl-2-[2-(3-phenylphenoxymethyl)phenyl]-2-methoxyiminoacetamide;
N-methyl-2-[2-(4-phenylphenoxymethyl)phenyl]-2-methoxyiminoacetamide;
N-methyl-2-[2-(2-isopropoxyphenoxymethyl)phenyl]-2-methoxyiminoacetamide;
N-methyl-2-[2-(4-isopropoxyphenoxymethyl)phenyl]-2-methoxyiminoacetamide;
N-methyl-2-{2-[2-(2-propynyloxy)phenoxymethyl]phenyl}-2-methoxyiminoacetamide;
N-methyl-2-{2-[3-(2-propynyloxy)phenoxymethyl]phenyl}-2-methoxyiminoacetamide;
N-methyl-2-{2-[4-(2-propynyloxy)phenoxymethyl]phenyl}-2-methoxyiminoacetamide;
N,N-dimethyl-2-[2-(4-trifluoromethylthiophenoxymethyl)phenyl]-2-methoxyiminoacetamide;
N-methyl-2-[2-(2-fluorophenoxymethyl)phenyl]-2-methoxyiminoacetamide;
N,N-dimethyl-2-[2-(3-fluorophenoxymethyl)phenyl]-2-methoxyiminoacetamide;
N-methyl-2-[2-(2-trifluoromethylphenoxymethyl)phenyl]-2-methoxyiminoacetamide;
N-methyl-2-[2-(4-trifluoromethylphenoxymethyl)phenyl]-2-methoxyiminoacetamide;

N-methyl-2-[2-(2,3-dimethylphenoxymethyl)phenyl]-2-methoxyiminoacetamide;
N-methyl-2-[2-(2,4-dimethylphenoxymethyl)phenyl]-2-methoxyiminoacetamide;
N-methyl-2-[2-(2,5-dimethylphenoxymethyl)phenyl]-2-methoxyiminoacetamide;
N-methyl-2-[2-(2,6-dimethylphenoxymethyl)phenyl]-2-methoxyiminoacetamide;
N-methyl-2-[2-(3,4-dimethylphenoxymethyl)phenyl]-2-methoxyiminoacetamide;
N-methyl-2-[2-(3,5-dimethylphenoxymethyl)phenyl]-2-methoxyiminoacetamide;
N-methyl-2-[2-(indan-5-yloxymethyl)phenyl]-2-methoxyiminoacetamide;
N-methyl-2-[2-(2,3-difluorophenoxymethyl)phenyl]-2-methoxyiminoacetamide;
N-methyl-2-[2-(2,5-difluorophenoxymethyl)phenyl]-2-methoxyiminoacetamide;
N-methyl-2-[2-(2,6-difluorophenoxymethyl)phenyl]-2-methoxyiminoacetamide;
N-methyl-2-[2-(3,4-difluorophenoxymethyl)phenyl]2-methoxyiminoacetamide;
N-methyl-2-[2-(3,5-difluorophenoxymethyl)phenyl]-2-methoxyiminoacetamide;
N-methyl-2-[2-(2,3-dichlorophenoxymethyl)phenyl]-2-methoxyiminoacetamide;
N-methyl-2-[2-(2,5-dichlorophenoxymethyl)phenyl]-2-methoxyiminoacetamide;
N-methyl-2-[2-(2,6-dichlorophenoxymethyl)phenyl]-2-methoxyiminoacetamide;
N-methyl-2-[2-(4-chloro-2-methylphenoxymethyl)phenyl]-2-methoxyiminoacetamide;
N-methyl-2-[2-(4-chloro-3-methylphenoxymethyl)phenyl]-2-methoxyiminoacetamide;
N-methyl-2-[2-(4-chloro-3-ethylphenoxymethyl)phenyl]-2-methoxyiminoacetamide;
N-methyl-2-[2-(3-chloro-5-methoxyphenoxymethyl)phenyl]-2-methoxyiminoacetamide;
N-methyl-2-[2-(2,3,5-trimethylphenoxymethyl)phenyl]-2-methoxyiminoacetamide;
N-methyl-2-[2-(2,3,6-trimethylphenoxymethyl)phenyl]-2-methoxyimmnoacetamide;
N-methyl-2-[2-(2,4,6-trimethylphenoxymethyl)phenyl]-2-methoxyiminoacetamide;
N-methyl-2-[2-(2,4,5-trichlorophenoxymethyl)phenyl]-2-methoxyimmnoacetamide;
N-methyl-2-[2-(2,4,6-trichlorophenoxymethyl)phenyl]-2-methoxyiminoacetamide;
N-methyl-2-[2-(2,3,5-trichlorophenoxymethyl)phenyl]-2-methoxyiminoacetamide;
N-methyl-2-[2-(2,3,6-trichlorophenoxymethyl)phenyl]-2-methoxyiminoacetamide;
N-methyl-2-[2-(4-chloro-3,5-dimethylphenoxymethyl)phenyl]-2-methoxyiminoacetamide;
N-methyl-2-[2-(2-chloro-4,5-dimethylphenoxymethyl)phenyl]-2-methoxyiminoacetamide;
N-methyl-2-[2-(2,3,5,6-tetrafluorophenoxymethyl)phenyl]-2-methoxyiminoacetamide;
N-methyl-2-[2-(2,3,4,5,6-pentafluorophenoxymethyl)phenyl]-2-methoxyiminoacetamide;
N-methyl-2-[2-(3-chloro-5-trifluoromethylpyridin-2-yloxymethyl)phenyl]-2-methoxyiminoacetamide;
N-methyl-2-[2-(3,5-dichloropyridin-2-yloxymethyl)phenyl]-2-methoxyiminoacetamide;
N-methyl-2-[2-(6-chloropyridin-2-yloxymethyl)phenyl]-2-methoxyiminoacetamide;
N-methyl-2-[2-(6-chloro-3-trifluoromethylpyridin-2-yloxymethyl)phenyl]-2-methoxyiminoacetamide;
N-methyl-2-[2-(6-chloro-5-trifluoromethylpyridin-2-yloxymethyl)phenyl]-2-methoxyiminoacetamide;
N-methyl-2-[2-(2-benzothiazolyloxymethyl)phenyl]-2-methoxyiminoacetamide;
N-methyl-2-[2-(2-benzoxazolyloxymethyl)phenyl]-2-methoxyiminoacetamide;
N-methyl-2-[2-(7-coumarinyloxymethyl)phenyl]-2-methoxyiminoacetamide;
N-methyl-2-[2-(1-naphthyloxymethyl)phenyl]-2-methoxyiminoacetamide;
N-methyl-2-[2-(2-naphthyloxymethyl)phenyl]-2-methoxyiminoacetamide;
N-methyl-2-[2-(4-chloro-1-naphthyloxymethyl)phenyl]-2-methoxyiminoacetamide;
N-methyl-2-[2-(6-bromo-2-naphthyloxymethyl)phenyl]-2-methoxyiminoacetamide;
N-methyl-2-[2-(2-methyl-l-naphthyloxymethyl)phenyl]-2-methoxyiminoacetamide;
N-methyl-2-[2-(1-bromo-2-naphthyloxymethyl)phenyl]-2-methoxyiminoacetamide;
N-methyl-2-[2-(3-allyloxyphenoxy)phenyl]-2-methoxyiminoacetamide;
N-methyl-2-[2-(3-cyanomethoxyphenoxy)phenyl]-2-methoxyiminoacetamide;
N-methyl-2-[2-(3-trifluoromethylphenoxy)phenyl]-2-methoxyiminoacetamide;
N-methyl-2-[2-(4-fluorophenoxy)phenyl]-2-methoxyiminoacetamide;
N-methyl-2-[2-(2,5-dimethylphenoxy)phenyl]-2-methoxyiminoacetamide;
N-methyl-2-[2-(4-chloro-3-methylphenoxy)phenyl]-2-methoxyiminoacetamide;
N-methyl-2-[2-(3,4-dimethylphenoxy)phenyl]-2-methoxyiminoacetamide;
N-methyl-2-[2-(3,5-dimethylphenoxy)phenyl]-2-methoxyiminoacetamide;
N-methyl-2-[2-(2,3-dimethylphenoxy)phenyl]-2-methoxyiminoacetamide;
N-methyl-2-[2-(2,4-dimethylphenoxy)phenyl]-2-methoxyiminoacetamide;
N-methyl-2-[2-(2,3,4-trimethylphenoxy)phenyl]-2-methoxyiminoacetamide;
N-methyl-2-[2-(3,4,5-trimethylphenoxy)phenyl]-2-methoxyiminoacetamide;
N-methyl-2-[2-(4-fluorophenoxymethyl)phenyl]-2-methoxyiminoacetamide;
N-methyl-2-[2-(2,4-difluorophenoxymethyl)phenyl]-2-methoxyiminoacetamide;
N-methyl-2-[2-(2-methylphenoxymethyl)phenyl]-2-methoxyiminoacetamide;
N-methyl-2-[2-(3-methylphenoxymethyl)phenyl]-2-methoxyiminoacetamide;
N-methyl-2-[2-(6-methoxypyridin-2-yloxymethyl)phenyl]-2-methoxyiminoacetamide;
N-methyl-2-[2-(3,6-dichloro-5-trifluoromethylpyridin-2-yloxymethyl)phenyl]-2-methoxyiminoacetamide;
N-methyl-2-[2-(5-trifluoromethylpyridin-2yloxymethyl)phenyl]-2-methoxyiminoacetamide;
N-methyl-2-[2-(3-trifluoromethylpyridin-2yloxymethyl)phenyl]-2-methoxyiminoacetamide;
N-methyl-2-[2-(6-trifluoromethylpyridin-2yloxymethyl)phenyl]-2-methoxyiminoacetamide;
N-methyl-2-[2-(5-chloro-3-trifluoromethylpyridin-2-yloxymethyl)phenyl]-2-methoxyiminoacetamide;
N-methyl-2-[2-(6-methylthiopyridin-2-yloxymethyl)phenyl]-2-methoxyiminoacetamide;
N-methyl-2-[2-(6-isopropoxypyridin-2-yloxymethyl)phenyl]-2-methoxyiminoacetamide;

N-methyl-2-[2-(6-methoxy-3-trifluoromethylpyridin-2-yloxymethyl)phenyl]-2-methoxyiminoacetamide;

N-methyl-2-[2-(6-methylthio-3-trifluoromethylpyridin-2-yloxymethyl)phenyl]-2-methoxyiminoacetamide;

N-methyl-2-[2-(6-isopropoxy-3-trifluoromethylpyridin-2-yloxymethyl)phenyl]-2-methoxyiminoacetamide;

N-methyl-2-[2-(6-methoxy-5-trifluoromethylpyridin-2-yloxymethyl)phenyl]-2-methoxyiminoacetamide;

N-methyl-2-[2-(6-isopropoxy-5-trifluoromethylpyridin-2-yloxymethyl)phenyl]-2-methoxyiminoacetamide;

N-methyl-2-[2-(6-methylthio-5-trifluoromethylpyridin-2-yloxymethyl)phenyl]-2-methoxyiminoacetamide;

N-methyl-2-[2-(2-chloropyridin-3-yloxymethyl)phenyl]-2-methoxyiminoacetamide.

In a preferred process embodying the present invention, the compound (I) can be prepared according to the following steps.

Step 1: Conversion of the compound (II) into the compound (III):

The compound (II) is treated with a base in a solvent to give a salt of the compound (III).

Examples of the base include alkaline or alkaline earth metal hydroxides (e,g, sodium hydroxide, potassium hydroxide, etc.), alkaline or alkaline earth metal carbonates (e.g., sodium carbonate, potassium carbonate, etc.), alkaline or alkaline earth metal alkoxides (e.g., sodium methoxide, sodium ethoxide, potassium t-butoxide, etc.) and the like. The amount of the base to be used is normally 1 to 20 mol, preferably 1 to 3 mol per mol of the compound (II).

Examples of the solvent include N,N-dimethyl-formamide, dimethyl sulfoxide, hydrocarbons (e.g., toluene, benzene, xylene, cyclohexane, hexane, etc.), alcohols (e.g., methanol, ethanol, isopropanol, butanol, etc.), ethers (e.g., tetrahydrofuran, dioxane, etc.), water and the like. These solvents can be used alone or as mixtures thereof.

The reaction temperature is normally 20° to 200° C., preferably 50° to 180° C. The reaction time is 0.5 to 100 hours, preferably 1 to 48 hours.

The salt of the compound (III) thus obtained can be used in the next step as the reaction mixture or the crude product, or after purification by conventional methods. If necessary, the compound (III) may be isolated from its salt, for example, by treatment of the salt with an appropriate acid optionally after removal of impurities by washing the salt with an appropriate organic solvent. Examples of the acid include hydrohalogenic acids (e.g., hydrochloric acid, hydrobromic acid, etc,), sulfuric acid, sulfonic acids (e.g., trifluoromethanesulfonic acid, toluenesulfonic acid, etc.) and the like.

Step 2: Conversion of the compound (III) into the compound (IV):

The compound (III) is reacted with a halogenating agent in the absence of a solvent or in an appropriate solvent in the presence or absence of a catalyst to give the compound (IV).

Examples of the halogenating agent include thionyl chloride, phosphoryl chloride, phosphorus pentachloride, phosphorus trichloride, phosgene, thionyl bromide, phosphoryl bromide, phosphorus pentabromide, phosphorus tribromide, oxalyl chloride and the like. The amount of the halogenating agent to be used is normally 1 to 10 mol, preferably 1 to 3 mol per mol of the compound (III). Slow addition of the halogenating agent is preferred because it increases the E-isomer content.

The catalyst is not necessarily used. When it is used, it can appropriately be selected from N,N-dimethyl-formamide, dimethyl sulfoxide, hexamethylphosphoric triamide, pyridine, triethylamine, iodine, zinc chloride, Vilsmeyer reagent and the like. The amount of the catalyst to be used is normally 0.005 to 10 mol, preferably 0.01 to 1 mol per mol of the compound (III).

The solvent is not necessarily used. When it is used, hydrocarbons (e.g., toluene, benzene, xylene, hexane, cyclohexane, etc.), halogenated hydrocarbons (e.g., methylene chloride, dichloroethane, etc.) and the like can be used alone or as mixtures thereof.

The reaction temperature is generally −50° to 160° C., preferably 0° to 120° C. The reaction time is normally 0.2 to 48 hours, preferably 0.5 to 24 hours.

The compound (IV) thus obtained can be used in the next step as the reaction mixture or the crude product, or after purification by conventional methods.

Step 3: Conversion of the compound (IV) to the compound (I):

The compound (IV) is reacted with an amine in the absence of a solvent or in an appropriate solvent in the presence or absence of a base to give the compound (I).

The amine is a compound of the formula: $HNR^1R^2$ (wherein $R^1$ and $R^1$ are as defined above) and may be primary amines, secondary amines or ammonia. Examples of the primary amines or secondary amines include lower alkylamines or di(lower)alkylamines each having lower alkyl described above for $R^1$ and $R^2$. The amount of the amine to be used is normally 1 to 20 mol, preferably 1 to 5 mol per mol of the compound (IV).

The base may be used to trap the resulting acid. Alternatively, an excess amount of the above amine as the reagent can be used in place of the base. When the base is used, it can be selected from pyridine, triethylamine, sodium hydroxide, potassium hydroxide, sodium carbonate, potassium carbonate, sodium methoxide, sodium ethoxide, potassium t-butoxide and the like. The amount of the base to be used is normally 1 to 20 mol, preferably 1 to 3 mol per mol of the compound (IV).

When a solvent is used, it can appropriately be selected from hydrocarbons (e.g., toluene, benzene, xylene, cyclohexane, hexane, etc.), halogenated hydrocarbons (e.g., methylene chloride, dichloroethane, etc.), ethers (e.g., tetrahydrofuran, dioxane, etc.), water and the like. These solvents can be used alone or as mixtures thereof. When the amine or base described above is liquid, it can also be used as the solvent.

The reaction temperature is normally −50° to 160° C., preferably 0° to 120° C. The reaction time is normally 0.1 to 24 hours, preferably 0.5 to 12 hours.

The alkoxyiminoacetamide compound (I) thus obtained is generally a mixture of the E- and Z-isomers. The mixture as it is can be used for agricultural fungicides. Since the E-isomer generally has superior fungicidal activity to that of the Z-isomer, the E-isomer content is preferably increased. In general, isomerization of Z-isomers to E-isomers proceeds under acidic conditions. Such isomerization may sometimes occur more or less in any of the above steps under acidic conditions. However, if necessary, the compound (I) obtained in the last step may optionally be treated with an acid for isomerization to increase the E-isomer content. In preferred embodiment of the present invention, the treatment with an acid is carried out. If necessary, the compound (I) may be separated and purified from the reaction mixture before the isomerization.

The isomerization with an acid can be carried out by treating the compound (I) with an acid in an appropriate solvent. Examples of the acid include hydrohalogenic acids (e.g., hydrochloric acid, hydrobromic acid, etc,), hydrogen halides (e.g., hydrogen chloride, hydrogen bromide, etc.), sulfonic acids (e.g., toluenesulfonic acid, etc.), thionyl chloride, oxalyl chloride, aluminium chloride, aluminium bromide, titanium trichloride, titanium tetrachloride and the like. These acids can be used alone or as mixtures thereof. The amount of the acid is normally 0.001 to 20 mol, preferably 0.01 to 2 mol per mol of the compound (I). Examples of the solvent include hydrocarbons benzene, toluene, xylene), halogenated hydrocarbons (e.g., methylene chloride, 1,2-dichloroethane, etc.), ethers (e.g., tetrahydrofuran, dioxane, etc.), ketones acetone, ethyl methyl ketone, etc.). Among them, hydrocarbons (e.g., benzene, etc.) and halogenated hydrocarbons (e.g., methylene chloride, 1,2-dichloroethane, etc.) are preferred. The reaction temperature is normally 0° to 150° C., preferably 20° to 110° C. The reaction time is normally 0.5 to 72 hours, preferably 1 to 24 hours.

The compound (II) used as the starting material in the above step 1 can be prepared according to the method described in Japanese Patent Application No. 5-273556. For example, the compound (II) wherein B is —OCH2— can be obtained according to the process of the following scheme.

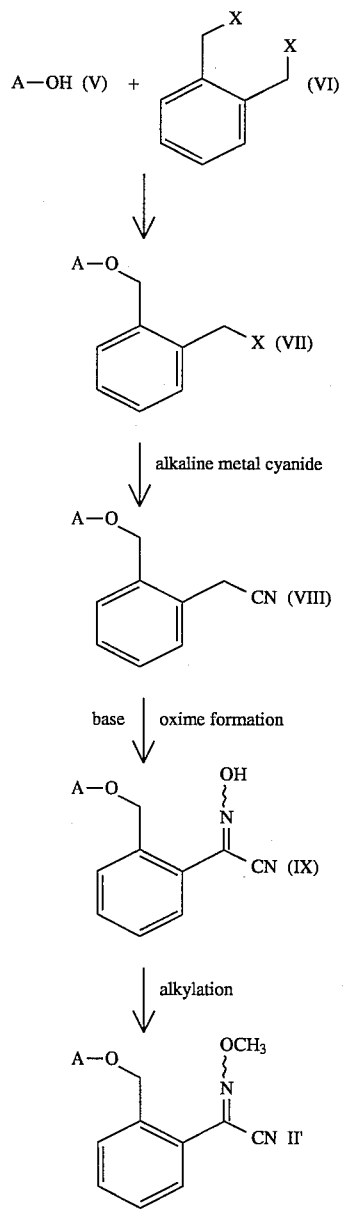

wherein each symbol is as defined above.

Firstly, the compound (V) is reacted with excess α,α'-o-dihalogenoxylene (VI) in an appropriate solvent in the presence of a base in the presence or absence of a phase-transfer catalyst.

Examples of the α,α'-o-dihalogenoxylene (VI) to be used include α,α'-o-dichloroxylene, α,α'-o-dibromoxylene, α,α'-o-diiodoxylene and the like. The amount of the α,α'-o-dihalogenoxylene (VI) to be used is 1 to 10 mol, preferably 3 to 5 mol per mol of the compound (V). When the reaction is carried out without using excess α,α'-o-dihalogenoxylene (VI), the compound (X) of the formula:

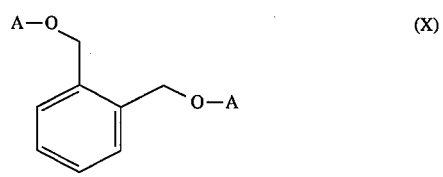

wherein each symbol is as defined above, is produced in a large amount.

Examples of the solvent to be used include the same solvents as those described for the above reaction using the alkaline metal cyanide. These solvents can be used alone or in combination thereof.

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 5 mol, preferably 1 to 2 mol per mol of the compound (V).

Examples of the phase-transfer catalyst include the same phase-transfer catalysts as those described for the above reaction using the alkaline metal cyanide. The amount of the phase-transfer catalyst to be used is 0.01 to 0.2 mol, preferably 0.05 to 0.1 mol per mol of the compound (V).

The reaction temperature is 0° to 120° C., preferably 20° to 100° C. The reaction time is 20 minutes to 12 hours, preferably 30 minutes to 3 hours.

The remaining α,α'-o-dihalogenoxylene (VI) is removed from the crude benzyl halide (VII) thus obtained. The resulting residue can be used in the next step as it is or after purification by conventional methods.

Then, the benzyl halide (VII) is reacted with an alkaline metal cyanide in an appropriate solvent in the presence or absence of a phase-transfer catalyst to obtain the benzyl cyanide (VIII).

Examples of the alkaline metal cyanide to be used include sodium cyanide, potassium cyanide and the like. The amount of the alkaline metal cyanide to be used is 1 to 5 mol, preferably 1 to 2 mol per mol of the benzyl halide (VII).

Examples of the solvent to be used include acetone, acetonitrile, methyl ethyl ketone, dimethyl-formamide (DMF), dimethyl sulfoxide (DMSO), toluene, methanol, ethanol, isopropanol, butanol, tetrahydrofuran (THF), dioxane, water and the like. These solvents can be used alone or in combination thereof.

Examples of the phase-transfer catalyst include tetra-n-butylammonium chloride, tetra-n-butylammonium bromide, tetra-n-butylammonium hydrogensulfate, tetramethylammonium bromide, benzyltriethylammonium chloride, tris(3,6-dioxaheptyl)amine and the like. The amount of the phase-transfer catalyst to be used is 0.01 to 0.2 mol, preferably 0.05 to 0.1 mol per mol of the benzyl halide The reaction temperature is 0° to 120° C., preferably 20° to 100° C. The reaction time is 10 minutes to 24 hours, preferably 30 minutes to 5 hours.

The benzyl cyanide (VIII) thus obtained can be used in the next step as the reaction mixture or the crude product, or after purification by conventional methods.

Then, the above benzyl cyanide (VIII) is reacted with an alkyl nitrite for formation of an oxime in an appropriate solvent in the presence of a base in the presence or absence of a phase-transfer catalyst to obtain α-hydroxyiminobenzyl cyanide (IX).

Examples of the alkyl nitrite to be used include methyl nitrite, ethyl nitrite, propyl nitrite, isopropyl nitrite, butyl nitrite, isoamyl nitrite and the like. The amount of the alkyl nitrite to be used is 1 to 5 mol, preferably 1 to 2 mol per mol of the benzyl cyanide (VIII).

Examples of the solvent to be used include the same solvents as those described for the above reaction using the alkaline metal cyanide. These solvents can be used alone or in combination thereof.

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 5 mol, preferably 1 to 2 mol per mol of the benzyl cyanide (VIII).

Examples of the phase-transfer catalyst include the same phase-transfer catalysts as those described for the above reaction using the alkaline metal cyanide. The amount of the phase-transfer catalyst to be used is 0.01 to 0.2 mol, preferably 0.05 to 0.1 mol per mol of the benzyl cyanide (VIII).

The reaction temperature is 0° to 120° C., preferably 20° to 50° C. The reaction time is 5 minutes to 12 hours, preferably 30 minutes to 3 hours.

The α-hydroxyiminobenzyl cyanide (IX) thus obtained can be used in the next step as the reaction mixture or the crude product, or after purification by conventional methods.

Then, the above α-hydroxyiminobenzyl cyanide (IX) is reacted with an alkylating agent in an appropriate solvent in the presence of a base in the presence or absence of a phase-transfer catalyst to obtain α-alkoxyiminobenzyl cyanide (II').

Examples of the alkylating agent to be used include dialkyl sulfates (e.g., dimethyl sulfate, etc.), alkyl halides (e.g., methyl chloride, methyl bromide, methyl iodide, etc.) and the like. The amount of the alkylating agent to be used is 1 to 5 mol, preferably 1 to 2 mol per mol of the a-hydroxyiminobenzyl cyanide (IX).

Examples of the base to be used include sodium hydroxide, potassium hydroxide, sodium carbonate, potassium carbonate, sodium methoxide, sodium ethoxide, potassium tert-butoxide and the like. The amount of the base to be used is 1 to 5 mol, preferably 1 to 2 mol per mol of the α-hydroxyiminobenzyl cyanide (IX).

Examples of the solvent to be used include the same solvents as those described for the above reaction using the alkaline metal cyanide. These solvents can be used alone or in combination thereof.

Examples of the phase-transfer catalyst include the same phase-transfer catalysts as those described for the above reaction using the alkaline metal cyanide. The amount of the phase-transfer catalyst to be used is 0.01 to 0.2 mol, preferably 0.05 to 0.1 mol per mol of the α-hydroxyiminobenzyl cyanide (IX).

The reaction temperature is 0° to 120° C., preferably 0° to 30° C. The reaction time is 5 minutes to 12 hours, preferably 15 minutes to 2 hours.

Alternatively, the benzyl cyanide (VIII) is reacted with an alkyl nitrite under the same conditions as those described for the conversion of the compound (VIII) to the compound (IX). Then, an alkylating agent is added to the reaction mixture for the alkylation. Thus, α-alkoxyiminobenzyl cyanide (II') can be obtained by one-pot synthesis.

The α-alkoxyiminobenzyl cyanide thus obtained can be used in the next step as the reaction mixture or the crude product, or after purification by conventional methods.

The alkoxyiminoacetamide (I) obtained by the process of the present invention can be used as agricultural fungicides, for example, according to the method described in U.S. Pat. No. 5185342.

As described hereinabove, according to the present invention, there is provided a process for producing alkoxyiminoacetamide compound (I). This process gives the compound in high yield. Further, since the content of the desired compound, particularly its E-isomer, in the end product is high, the compound can easily be purified and has excellent fungicidal activity.

The following examples further illustrate the present invention in detail but are not to be construed to limit the scope thereof.

EXAMPLE 1

Synthesis of 2-(2,5-dimethylphenoxymethyl)benzyl chloride

Potassium carbonate (55.28 g, 0.4 mol), α,α'-o-dichloroxylene (175.06 g, 1.0 mol) and acetone (200 ml) were added to 2,5-xylenol (24.43 g, 0.2 mol). The mixture was heated under reflux for 8 hours. After completion of the reaction, the resulting insoluble materials were removed, and excess α,α'-o-dichloroxylene was evaporated under reduced pressure to obtain 2-(2,5-dimethylphenoxymethyl)benzyl chloride (53.20 g, Yield: 88.5%, Purity: 86.8%) as a colorless oil.

EXAMPLE 2

Synthesis of 2-(2,5-dimethylphenoxymethyl)benzyl chloride

95% sodium hydroxide (13.89 g, 0.33 mol) and water (60 ml) were added to 2,5-xylenol (36.65 g, 0.3 mol) and dissolved while heating. Then water was evaporated under reduced pressure. α,α'-o-Dichloroxylene (105.04 g, 0.6 mol) and acetone (150 ml) were added to the resulting sodium salt, and the mixture was heated under reflux for 1 hour. After completion of the reaction, the resulting insoluble materials were removed. After distillation under reduced pressure, 2-(2,5-dimethylphenoxymethyl)benzyl chloride (39.07 g, Yield: 49.9%) was obtained as colorless crystals.

bp 145°–147° C./0.6 mmHg, mp 46.5°–48.5° C.

$^1$H-NMR (CDCl$_3$) δppm: 2.21(s,3H), 2.34(s,3H), 4.74(s, 2H), 5.18(s,2H), 6.71–7.54(m,7H).

EXAMPLE 3

Synthesis of 2-(2,5-dimethylphenoxymethyl)benzyl cyanide 2-(2,5-Dimethylphenoxymethyl)benzyl chloride (Purity: 86.8%, 1.50 g, 5 mmol), 95% sodium cyanide (0.31 g, 6 mmol), triethylbenzylammonium chloride (0.06 g, 0.25 mmol), acetone (4 ml) and water (2 ml) were added. The mixture was heated under reflux for 5 hours. After completion of the reaction, water (100 ml) was added. The resulting mixture was extracted with ether (100 ml), dried over anhydrous magnesium sulfate and concentrated under reduced pressure. The resulting residue was purified by silica gel chromatography (ethyl acetate/n-hexane) to give 2-(2,5-dimethylphenoxymethyl)benzyl cyanide (1.23 g, Yield: 97.8%).

mp 51.5°–53° C.

¹H-NMR(CDCl₃) δppm: 2.18(s,3H), 2.34(s,3H), 3.89(s, 2H), 5.05(s,2H), 6.72–7.52(m,7H).

EXAMPLE 4

Synthesis of 2-(2,5-dimethylphenoxymethyl)-α-hydroxyiminobenzyl cyanide

85% Potassium hydroxide (0.40 g, 6 mmol), toluene (5 ml) and butyl nitrite (0.62 g, 6 mmol) were added to 2-(2,5-dimethylphenoxymethyl)benzyl cyanide (1.26 g, 5 mmol). The mixture was stirred at room temperature for 8 hours. After completion of the reaction, water (100 ml) was added. The mixture was neutralized with hydrochloric acid, extracted with ether (100 ml), dried over anhydrous magnesium sulfate and concentrated under reduced pressure. The resulting residue was purified by silica gel chromatography (ethyl acetate/n-hexane) to give 2-(2,5-dimethylphenoxymethyl)-α-hydroxyiminobenzyl cyanide (1.30 g, Yield: 92.8%, E/Z=15/85).

A part of it was taken and separated into the E- and Z-isomers, and the physical properties were determined.

E-isomer:
mp 114°–115° C.
¹H-NMR (CDCl₃) δppm: 2.23 (s,3H), 2.31(s,3H), 5.06 (s,2H), 6.65–7.66(m,7H), 8.41(s,1H).

Z-isomer:
mp 150.5°–151.5° C.
¹H-NMR (CDCl₃) δppm: 2.24(s,3H), 2.31(s,3H), 5.24(s, 2H), 6.64–7.79(m,7H), 8.68(s,1H).

EXAMPLE 5

Synthesis of 2-(2,5-dimethylphenoxymethyl)-α-methoxyiminobenzyl cyanide

Potassium carbonate (3.32 g, 0.024 mol) and acetone (200 ml) were added to 2-(2,5-dimethylphenoxymethyl)-α-hydroxyiminobenzyl cyanide (E/Z=15/85) (5.61 g, 0.02 mol). The mixture was stirred for 5 minutes. Then dimethyl sulfate (3.03 g, 0.024 mol) was added, and the mixture was stirred at room temperature for 18 hours. After completion of the reaction, the resulting insoluble materials were removed. To the residue obtained after evaporation under reduced pressure, toluene (50 ml) and 1N aqueous sodium hydroxide solution (50 ml) were added. The mixture was stirred for 1 hour. After stirring, water (150 ml) was added. The mixture was extracted with ether (150 ml), dried over anhydrous magnesium sulfate and concentrated under reduced pressure. The resulting residue was purified by silica gel chromatography (ethyl acetate/n-hexane) to give 2-(2,5-dimethylphenoxymethyl)-α-methoxyiminobenzyl cyanide (5.44 g, Yield: 92.4%, E/Z=15/85).

A part of it was taken and separated into the E- and Z-isomers, and the physical properties were determined.

E-isomer: Colorless oil.
¹H-NMR (CDCl₃) δppm: 2.23 (s,3H), 2.31(s,3H), 4.04 (s,3H), 5.01(s,2H), 6.63–7.63(m,7H).

Z-isomer: Colorless crystals.
mp 107°–108° C.
¹H-NMR (CDCl₃) δppm: 2.24(s,3H), 2.30(s,3H), 4.13(s, 2H), 5.26(s,2H), 6.62–7.76(m,7H).

EXAMPLE 6

Synthesis of 2-(2,5-dimethylphenoxymethyl)-α-methoxyiminobenzyl cyanide

95% Sodium hydroxide (0.32 g, 7.5 mmol), acetone (5 ml) and butyl nitrite (0.62 g, 6 mmol) were added to 2-(2,5-dimethylphenoxymethyl)benzyl cyanide (1.26 g, 5 mmol). The mixture was stirred at room temperature for 2 hours. Dimethyl sulfate (0.95 g, 7.5 mmol) was added, and the mixture was stirred under ice-cooling for 10 minutes and at room temperature for 1 hour. After completion of the reaction, toluene (10 ml) and 1N aqueous sodium hydroxide solution (10 ml) were added, and the mixture was stirred at room temperature for 1 hour. After stirring, water (100 ml) was added. The mixture was extracted with ether (100 ml), dried over anhydrous magnesium sulfate and concentrated under reduced pressure. The resulting residue was purified by silica gel chromatography (ethyl acetate/n-hexane) to give 2-(2,5-dimethylphenoxymethyl)-α-methoxyiminobenzyl cyanide (1.29 g, Yield: 87.6%, E/Z=13/87).

EXAMPLE 7

Synthesis of (Z)-2-[2-(2,5-dimethylphenoxymethyl)phenyl]- 2-methoxyiminoacetic acid To (Z)-2-(2,5-dimethylphenoxymethyl)-α-methoxyiminobenzyl cyanide (0.59 g, 2 mmol) were added 85% potassium hydroxide (0.26 g, 4 mmol), butanol (4 ml) and water (0.4 ml). The mixture was stirred under reflux for 7 hours. After completion of the reaction, water (100 ml) was added. The resulting mixture was adjusted to pH of not more than 3 by adding 6N aqueous hydrochloric acid solution, extracted with methylene chloride (50 ml) twice, dried over anhydrous magnesium sulfate and concentrated under reduced pressure to give crystals (0.60 g), which were then recrystallized from n-hexane to give (Z)-2-[2-(2,5-dimethylphenoxymethyl)phenyl]-2-methoxyiminoacetic acid (0.42 g, Yield: 67.0%).

mp: 112.5°–113.5° C.
¹H-NMR (CDCl₃) δppm: 2.21(3H, s), 2.29(3H, s), 2.65(1H,brs), 4.09(3H, s), 5.20(2H, s), 6.64–7.63(7H,m).

EXAMPLE 8

Synthesis of 2-[2-(2,5-dimethylphenoxymethyl)phenyl]-2-methoxyiminoacetic acid

To 2-(2,5-dimethylphenoxymethyl)-α-methoxyiminobenzyl cyanide (E/Z=13/87)(2.94 g, 10 mmol) were added 96.7% potassium hydroxide (1.16 g, 20 mmol), butanol (20 ml) and water (2 ml). The mixture was stirred under reflux for 13 hours. After completion of the reaction, 1N aqueous hydrochloric acid solution (150 ml) was added. The mixture was extracted with toluene (150 ml), washed with water (100 ml), dried over anhydrous magnesium sulfate and concentrated under reduced pressure to give crude 2-[2-(2, 5-dimethylphenoxymethyl)phenyl]-2-methoxyiminoacetic acid (2.99 g, Yield 95.5%, Z=at least 99%).

EXAMPLE 9

Synthesis of 2-[2-(2,5-dimethylphenoxymethyl)phenyl]-2-methoxyimino-N-methylacetamide Toluene (10 ml), thionyl chloride (1.36 g, 11 mmol) and dimethylformamide (DMF) (0.1 ml) were added to the crude 2-[2-(2,5-dimethylphenoxymethyl)phenyl]-2-methoxyiminoacetic acid (Z=at least 99%)(2.99 g, 9.5 mmol), and the mixture was stirred at 70° C. for 1.5 hours. After completion of the reaction, the mixture was concentrated to give crude 2-[2-(2,5-dimethylphenoxymethyl)phenyl]-2-methoxyiminoacetyl chloride (E/Z=75/25).

¹H-NMR (CDCl₃) δppm: 2.18(2.25H, s), 2.27(0.75H, s), 2.29(2.25H, s), 2.32(0.75H, s), 4.04(0.75H, s), 4.12(2.25H, s), 4.88(1.5H, s), 5.26(0.5H, s), 6.67–7.57(7H,m).

The resulting crude product was dissolved in dry toluene (10 ml), the solution was added dropwise to a suspension of 40% aqueous methylamine solution (2.96 g, 38 mmol) and toluene (10 ml) under ice-cooling over 20 minutes, and the mixture was stirred at room temperature for 2 hours. After completion of the reaction, water (100 ml) was added. The resulting mixture was adjusted to pH of not more than 3 by adding 6N aqueous hydrochloric acid solution, extracted with ether (150 ml), dried over anhydrous magnesium sulfate and concentrated under reduced pressure. The resulting residue was purified by silica gel chromatography (ethyl acetate/n-hexane) to give 2-[2-(2,5-dimethylphenoxymethyl)phenyl]-2-methoxyimino-N-methylacetamide (2.64 g, Yield: 84.8%, E/Z=75/25).

EXAMPLE 10

Synthesis of (E)-2-[2-(2,5-dimethylphenoxymethyl)-phenyl]- 2-methoxyimino-N-methylacetamide Toluene (3 ml) and conc. hydrochloric acid (0.61 g, 6 mmol) were added to 2-[2-(2,5-dimethylphenoxymethyl)phenyl]-2-methoxyimino-N-methylacetamide (0.98 g, E/Z=75/25), and the mixture was stirred at 80° C. for 2 hours. After completion of the reaction, water (150 ml) was added. The mixture was extracted with methylene chloride (50 ml) twice, dried over anhydrous magnesium sulfate and concentrated under reduced pressure to give crystals (1.01 g, E/Z=95/5). The crystals were recrystallized from toluene to give (E)-2-[2-(2,5-dimethylphenoxymethyl)-phenyl]-2-methoxyimino-N-methylacetamide (0.72 .g, Yield 71.5%) as colorless crystals.

mp: 136°–137° C.

$^1$H-NMR (CDCl$_3$) δppm: 2.18(3H, s), 2.29(3H, s), 2.88(3H,d,J=4.9Hz), 3.95(3H,s), 4.92(2H,s), 6.62–7.57(8H, m).

EXAMPLES 11 to 14

Synthesis of 2-[2-(2,5-dimethylphenoxymethyl)phenyl]-2-methoxyiminoacetic acid

To 2-(2,5-dimethylphenoxymethyl)-α-methoxyiminobenzyl cyanide (E/Z=13/87)(2.94 g, 10 mmol) were added 96.7% potassium hydroxide (1.16 g, 20 mmol) and a solvent shown in Table 1. The mixture was subjected to reaction under conditions shown in Table 1. After completion of the reaction, 1N aqueous hydrochloric acid solution (150 ml) was added. The mixture was extracted with toluene (150 ml), washed with water (100 ml), dried over anhydrous magnesium sulfate and concentrated under reduced pressure to give crude 2-[2-(2,5dimethylphenoxymethyl)phenyl]-2-methoxyiminoacetic acid. The crude product was subjected to HPLC analysis to calculate the yield.

TABLE 1

| Example | Solvent (liter/mol) | Reaction conditions | Yield (%) | E/Z ratio |
|---|---|---|---|---|
| 11 | PhMe (2.0)/ MeOH (0.2) | reflux, 13 h | 52 | 59/41 |
| 12 | PhMe (2.0)/ H$_2$O (0.2)/ MeOH (0.2) | reflux, 20 h | 76 | 26/74 |
| 13 | MeOH (1.0)/ H$_2$O (0.5) | reflux, 22 h (internal tem-) perature: 74° C.) | 90 | 10/90 |
| 14 | PhMe (0.3)/ H$_2$O (0.5)/ MeOH (0.7) | reflux, 21 h (internal temperature: 74° C.) | 93 | 24/76 |

EXAMPLE 15

Synthesis of 2-[2-(2,5-dimethylphenoxymethyl)phenyl]-2-methoxyimino-N-methylacetamide 2-[2-(2,5-Dimethylphenoxymethyl)phenyl]-2-methoxyiminoacetic acid (9.40 g, 30 mmol, E/Z=20/80) was dissolved in dimethylformamide (DMF)(0.11 g, 1.5 mmol) and toluene (20 ml). A solution of 95% thionyl chloride (4.13 g, 33 mmol) and toluene (10 ml) was added dropwise at 60° C. over 5 hours. The mixture was stirred at 60° C. for 5 hours. After completion of the reaction, the mixture was concentrated under reduced pressure to a total amount of 30 g to give crude 2-[2-(2,5-dimethylphenoxymethyl)phenyl]-2-methoxyiminoacetyl chloride.

A half amount of the crude product thus obtained was added dropwise to a suspension of 40% aqueous methylamine solution (2.8 g, 36.1 mmol), water (10 g) and toluene (10 g) at 20° to 25° C. over 1 hour. The other half 10 of the crude product and 28.8% aqueous potassium hydroxide solution (4.2 g, 30 mmol) were added separately and simultaneously at 20° to 25° C. over 1 hour. The mixture was stirred at 20 to 25° C. for 1.5 hours. After completion of the reaction, the mixture was acidified by adding 1N aqueous hydrochloric acid solution (10 ml) and extracted with ethyl acetate (100 ml). The ethyl acetate layer was washed with saturated brine (150 ml) twice, dried over anhydrous sodium sulfate and concentrated under reduced pressure to give crystals of 2-[2-(2,5-dimethylphenoxymethyl)phenyl]-2-methoxyimino-N-methylacetamide (Purity: 95.4 %, determined by HPLC analysis)(9.81 g, Yield in terms of the pure product: 95.6%, E/Z=93/7).

EXAMPLE 16

Isomerization of 2-[2-(2,5-dimethylphenoxymethyl)-phenyl]-2-methoxyiminoacetamide (1) Toluene (5 ml) and thionyl chloride (0.12 g, 1 mmol) were added to 2-[2-(2,5-dimethylphenoxymethyl)phenyl]- 2-methoxyiminoacetamide (1.56 g, 5 mmol, E/Z= 9/91). The mixture was stirred at 80° C. for 8 hours. After completion of the reaction, water (50 ml) was added. The resulting mixture was extracted with toluene (50 ml) twice, 10 washed with 1N aqueous sodium hydroxide solution, water and saturated brine, and dried over anhydrous magnesium sulfate. The solvent was evaporated under reduced pressure to give colorless crystals (1.53 g)(Yield: 98%, E/Z=97/3).

(2) Toluene (5 ml) and titanium trichloride (25% diluted hydrochloric acid solution) (0.15 g, 0.25 mmol) were added to 2-[2-(2,5-dimethylphenoxymethyl)phenyl]-2-methoxyiminoacetamide (1.56 g, 5 mmol, E/Z=9/91). The mixture was stirred at 80° C. for 8 hours. After completion of the reaction, water (50 ml) was added. The resulting mixture was extracted with toluene (50 ml) twice, washed with 1N aqueous sodium hydroxide solution, water and saturated brine, and dried over anhydrous magnesium sulfate. The solvent was evaporated under reduced pressure to give pale orange crystals (1.51 g)(Yield: 97%, E/Z=96/4).

(3) Toluene (5 ml) and titanium tetrachloride (47 mg, 0.25 mmol) were added to 2-[2-(2,5-dimethylphenoxymethyl)-phenyl]- 2-methoxyiminoacetamide (1.56 g, 5 mmol, E/Z=9/91). The mixture was stirred at 80° C. for 24 hours. After completion of the reaction, water (50 ml) was added. The resulting mixture was extracted with toluene (50 ml) twice, washed with 1N aqueous sodium hydroxide solution, water and saturated brine, and dried over anhydrous magnesium sulfate. The solvent was evaporated under reduced pressure to give pale green crystals (1.56 g)(Yield: 100%, E/Z=97/3).

(4) Toluene (5 ml), titanium tetrachloride (47 mg, 0.25 mmol) and 5N hydrochloric acid (0.1 ml) were added to 2-[2-(2,5-dimethylphenoxymethyl)phenyl]-2-methoxyiminoacetamide (1.56 g, 5 mmol, E/Z=9/91). The mixture was stirred at 80° C. for 2 hours. After completion of the reaction, water (50 ml) was added. The resulting mixture was extracted with toluene (50 ml) twice, washed with 1N aqueous sodium hydroxide solution, water and saturated brine, and dried over anhydrous magnesium sulfate. The solvent was evaporated under reduced pressure to give pale brown crystals (1.55 g)(Yield: 99%, E/Z=97/3).

EXAMPLE 17

Synthesis of (E)-2-(2-chloro-3-pyridyloxymethyl)-α-methoxyiminophenylacetic acid Methanol (2 ml) and a 50% aqueous solution of potassium hydroxide (0.07 g, 0.66 mmol) were added to (E)-2-(2-chloro-3-pyridyloxymethyl)-a-methoxyiminophenylacetonitrile (0.11 g, 0.33 mmol). The mixture was stirred under reflux for 6 hours. After completion of the reaction, water (100 ml) was added, and the resulting 10 mixture was washed with methylene chloride (50 ml). Hydrochloric acid (1N, 1 ml) was added, and the mixture was extracted with methylene chloride (50 ml) twice. The methylene chloride layer was dried over anhydrous magnesium sulfate and evaporated under reduced pressure to dryness to give (E)-2-(2-chloro-3-pyridyloxymethyl)-α-methoxyiminophenylacetic acid (0.05 g, 42.8 %) as colorless crystals.

$^1$H-NMR(CDCl$_3$) δppm: 4.21(3H, s), 5.11(2H, s), 7.11–7.52(6H,m), 7.98–8.00(1H,m).

EXAMPLE 18

Synthesis of (E)-2-[2-(2-chloro-3-pyridyloxymethyl)phenyl]-2-methoxyimino-N-methylacetamide 1,2-Dichloroethane (1 ml), thionyl chloride (0.03 g, 0.28 mmol) and dimethylformamide (DMF)(0.01 ml) were added to (E)-2-(2-chloro-3-pyridyloxymethyl)-α-methoxyiminophenylacetic acid (0.05 g, 0.14 mmol). The mixture was stirred under reflux for 1 hour. To the reaction mixture was added 40% methylamine/methanol solution (1 ml) under ice-cooling. The mixture was stirred at 0° C. for 1 hour. After completion of the reaction, water (100 ml) was added, and the mixture was extracted with methylene chloride (50 ml) twice. The methylene chloride layer was dried over anhydrous magnesium sulfate and concentrated under reduced pressure. The resulting residue was purified by silica gel chromatography (ethyl acetate/n-hexane) to give (E)-2-[2-(2-chloro-3-pyridyloxymethyl)phenyl]-2-methoxyimino-N-methylacetamide (0.02 g, 42.8 %) as colorless crystals.

A part of them was recrystallized from ethyl acetate/n-hexane to give crystals (mp. 128°–129° C.).

$^1$H-NMR(CDCl$_3$) δppm: 2.90(3H,d,J=5.5), 3.94 (3H, s), 5.10(2H,s), 6.84(1H,brs), 7.11–7.53(6H,m), 7.95–7.97(1H, m).

What is claimed is:

1. A process for producing an (I): alkoxyiminoacetamide compound of the formula

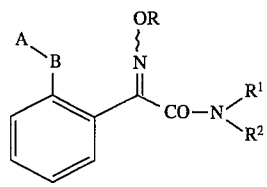

wherein A is hydrogen, lower alkyl, lower alkenyl, lower alkynyl, lower alkoxy, cyclo(lower)alkyl, cyclo(lower)alkenyl, optionally substituted phenyl or optionally substituted heterocyclic group, which when substituted has 1 to 5 substituents selected from the group consisting of lower alkyl, lower alkenyl, lower alkynyl, cycloalkyl, cycloalkenyl, lower alkanoyl, lower alkylsilyl, halogenated lower alkyl, di(lower)alkylamino, phenyl, phenyl(lower)alkyl, phenyl(lower)alkenyl, furyl(lower)alkyl, furyl(lower)alkenyl, halogen, nitro, cyano, —OR$^4$ (wherein R$^4$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzenesulfonyl or lower alkyl-benzenesulfonyl), and —CH$_2$—Z—R$^5$ (wherein Z is —O—, —S— or —NR$^6$— (wherein R$^5$ is hydrogen or lower alkyl), R$^5$ is phenyl, halophenyl, lower alkoxyphenyl, pyridyl or pyrimidinyl); B is —CH$_2$—, —O—, —S—, —CH(OH)—, —CO—, —NR$^3$— (wherein R$^3$ is hydrogen or lower alkyl), —CH$_2$CH$_2$, —CH=CH—, —C≡C—, —CH$_2$O—, —CH$_2$S—, —CH$_2$S(O)—, — OCH$_2$—, —SCH$_2$—, —S(O)CH$_2$— or epoxy; R is lower alkyl; R$^1$ and R$^2$ are each independently hydrogen or lower alkyl; and the bond denoted by — represents E-isomer, Z-isomer or a mixture of E- and Z-isomers; which comprises (a) halogenating a compound of the formula (III):

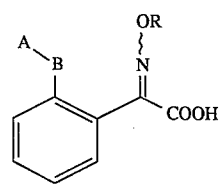

wherein each symbol is as defined above, to obtain a compound of the formula (IV):

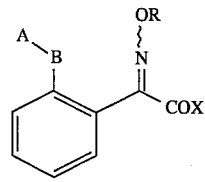

wherein X is halogen and the other symbols are as defined above, said halogenating being carried out by adding to the compound of formula (III) a halogenating agent selected from thionyl 2. A process according to claim 1, wherein step (c) is carried out with an acid selected from the group consisting of hydrohalogenic acids, hydrogen halides, sulfonic acids, thionyl chloride, oxalyl chloride, aluminium chloride, aluminium bromide, titanium trichloride, and titanium tetrachloride.

3. A process according to claim 1, wherein the compound of the formula (III) is obtained by reacting a compound of the formula (II):

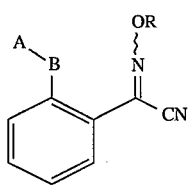

wherein each symbol is as defined in claim 1, with a base selected from the group consisting of hydroxides, carbonates, and alkoxides of an alkali or alkaline earth metal.

4. A process according to claim 3, wherein step (c) is carried out with an acid selected from the group consisting of hydrohalogenic acids, hydrogen halides, sulfonic acids, thionyl chloride, oxalyl chloride, aluminium chloride, aluminium bromide, titanium trichloride, and titanium tetrachloride.

5. A process according to claim 1, wherein A is optionally substituted phenyl, which when substituted has 1 to 5 substituents selected from the group consisting of lower alkyl, lower alkenyl, lower alkynyl, cycloalkyl, cycloalkenyl, lower alkanoyl, lower alkylsilyl, halogenated lower alkyl, di(lower)alkylamino, phenyl, phenyl(lower)alkyl, phenyl(lower)alkenyl, furyl(lower)alkyl, furyl(lower)alkenyl, halogen, nitro, cyano, —$OR^4$ (wherein $R^4$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzenesulfonyl or lower alkyl-benzenesulfonyl), and —$CH_2$—Z—$R^5$ (wherein Z is —O—, —S— or —$NR^6$— (wherein $R^6$ is hydrogen or lower alkyl), $R^5$ is phenyl, halophenyl, lower alkoxyphenyl, pyridyl or pyrimidinyl).

6. A process according to claim 5, wherein A is unsubstituted phenyl.

7. A process according to claim 5, wherein A is phenyl substituted with 1 to 5 substituents selected from the group consisting of lower alkyl and halogen.

8. A process according to claim 7, wherein A is phenyl substituted with 1 to 3 substituents selected from the group consisting of methyl, chlorine and fluorine.

9. A process according to claim 8, wherein A is 2,5-dimethylphenyl, 4-fluorophenyl, 4-chlorophenyl, 3,4-dimethylphenyl, 2-methylphenyl, 2-chlorophenyl, 2-methyl-4-chlorophenyl or 3,5-dimethylphenyl.

10. A process according to claim 1, wherein A is an optionally substituted heterocyclic group, which when substituted has 1 to 5 substituents selected from the group consisting of lower alkyl, lower alkenyl, lower alkynyl, cycloalkyl, cycloalkenyl, lower alkanoyl, lower alkylsilyl, halogenated lower alkyl, di(lower)alkylamino, phenyl, phenyl(lower)alkyl, phenyl(lower)alkenyl, furyl(lower)alkyl, furyl(lower)alkenyl, halogen, nitro, cyano, —$OR^4$ (wherein $R^4$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzenesulfonyl or lower alkyl-benzenesulfonyl), and —$CH_2$—Z—$R^5$ (wherein Z is —O—, —S— or —$NR^6$— (wherein $R^6$ is hydrogen or lower alkyl), $R^5$ is phenyl, halophenyl, lower alkoxyphenyl, pyridyl or pyrimidinyl).

11. A process according to claim 10, wherein A is optionally substituted pyridyl, which when substituted has 1 to 5 substituents selected from the group consisting of lower alkyl, lower alkenyl, lower alkynyl, cycloalkyl, cycloalkenyl, lower alkanoyl, lower alkylsilyl, halogenated lower alkyl, di(lower)alkylamino, phenyl, phenyl(lower)alkyl, phenyl(lower)alkenyl, furyl(lower)alkyl, furyl(lower)alkenyl, halogen, nitro, cyano, —$OR^4$ (wherein $R^4$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzenesulfonyl or lower alkyl-benzenesulfonyl), and —$CH_2$—Z—$R^5$ (wherein Z is —O—, —S— or —$NR^6$— (wherein $R^6$ is hydrogen or lower alkyl), $R^5$ is phenyl, halophenyl, lower alkoxyphenyl, pyridyl or pyrimidinyl).

12. A process according to claim 11, wherein A is pyridyl substituted with 1 to 5 substituents selected from the group consisting of halogen and halogenated lower alkyl.

13. A process according to claim 12, wherein A is pyridyl substituted with 1 to 5 substituents selected from the group consisting of chlorine and trifluoromethyl.

14. A process according to claim 13, wherein A is 5-trifluoromethylpyridyl, 5-chloro-3-trifluoromethylpyridyl or 6-chloro-3-trifluoromethylpyridyl.

15. A process according to claim 1, wherein B is —O—, —$CH_2O$— or —$OCH_2$—.

16. A process according to claim 1, wherein A is phenyl, 4-chlorophenyl, 4-fluorophenyl, 3,4-dimethylphenyl or 3,5-dimethylphenyl; B is —O—; R is methyl; $R^1$ is hydrogen; and $R^2$ is methyl.

17. A process according to claim 1, wherein A is 2-methylphenyl, 2-chlorophenyl, 4-chlorophenyl, 2,5-dimethylphenyl or 4-chloro-2-methylphenyl; B is —$OCH_2$—; R is methyl; $R^1$ is hydrogen; and $R^2$ is methyl.

18. A process according to claim 1, wherein A is 5-trifluoromethylpyridyl, 5-chloro-3-trifluoromethylpyridyl or 6-chloro-3-trifluoromethylpyridyl; B is —$OCH_2$—; R is methyl; $R^1$ is hydrogen; and $R^2$ is methyl.

19. A process according to claim 1, wherein the compound of the formula (I) is the E-isomer. chloride, phosphoryl chloride, phosphorus pentachloride, phosphorus trichloride, phosgene, thionyl bromide, phosphoryl bromide, phosphorus pentabromide, phosphorus tribromide, and oxalyl chloride over not less than 5 hours;

(b) reacting the compound of the formula (IV) with an amine of the formula $HNR^1R^1$ (wherein $R^1$ and $R^2$ are as defined above), to obtain a compound of the formula (I); and (c) optionally treating the compound of formula (I) with an acid.

20. A process for producing a compound of the formula (IV):

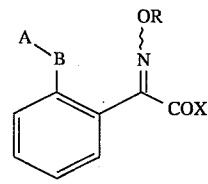

wherein A is hydrogen, lower alkyl, lower alkenyl, lower alkynyl, lower alkoxy, cyclo(lower)alkyl, cyclo(lower)alkenyl, optionally substituted phenyl or optionally substituted heterocyclic group, which when substituted has 1 to 5 substituents selected from the group consisting of lower alkyl, lower alkenyl, lower alkynyl, cycloalkyl, cycloalkenyl, lower alkanoyl, lower alkylsilyl, halogenated lower alkyl, di(lower)alkylamino, phenyl, phenyl(lower)alkyl, phenyl(lower)alkenyl, furyl(lower)alkyl, furyl(lower)alkenyl, halogen, nitro, cyano, —$OR^4$ (wherein $R^4$ is hydrogen, lower alkyl, lower alkenyl, lower alkynyl, lower alkanoyl, phenyl, lower alkoxyphenyl, nitrophenyl, phenyl(lower)alkyl, cyanophenyl(lower)alkyl, benzoyl, tetrahydropyranyl, pyridyl, trifluoromethylpyridyl, pyrimidinyl, benzothiazolyl, quinolyl, benzoyl(lower)alkyl, benzenesulfonyl or lower alkyl-benzenesulfonyl), and —CH$_2$—Z—R$^5$ (wherein Z is —O—, —S— or —NR$^6$— (wherein R$^6$ is hydrogen or lower alkyl), R$^5$ is phenyl, halophenyl, lower alkoxyphenyl, pyridyl or pyrimidinyl); B is —CH$_2$—, —O—, —S—, —CH(OH)—, —CO—, —NR$^3$— (wherein R$^3$ is hydrogen or lower alkyl), —CH$_2$CH$_2$, —CH=CH—, —C≡C—, —CH$_2$—, —CH$_2$S—, —CH$_2$S(O)—, — OCH$_2$—, —SCH$_2$—, —S(O)CH$_2$— or epoxy; R is lower alkyl; X is halogen; and the bond denoted by — represents E-isomer, Z-isomer or a mixture of E- and Z-isomers; which comprises halogenating a compound of the formula (III):

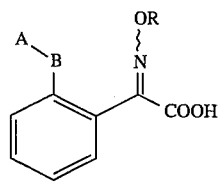

III wherein each symbol is as defined above, said halogenating being carried out by adding to the compound of formula (III) a halogenating agent selected from thionyl chloride, phosphoryl chloride, phosphorus pentachloride, phosphorus trichloride, phosgene, thionyl bromide, phosphoryl bromide, phosphorus pentabromide, phosphorus tribromide, and oxalyl chloride over not less than 5 hours.

* * * * *

UNITED STATES PATENT AND TRADEMARK OFFICE
CERTIFICATE OF CORRECTION

Page 1 of 2

PATENT NO. : 5,506,358
DATED : April 9, 1996
INVENTOR(S) : Akira TAKASE et al.

It is certified that error appears in the above-indentified patent and that said Letters Patent is hereby corrected as shown below:

Claim 1, column 22, line 34, change "denoted by -" to --denoted by ~--;

line 58, after "thionyl", insert --chloride, phosphoryl chloride, phosphorus pentachloride, phosphorus trichloride, phosgene, thionyl bromide, phosphoryl bromide, phosphorus pentabromide, phosphorus tribromide, and oxalyl chloride over not less than 5 hours;

(b) reacting the compound of the formula (IV) with an amine of the formula $HNR^1R^2$ (wherein $R^1$ and $R^2$ are as defined above), to obtain a compound of the formula (I); and (c) optionally treating the compound of formula (I) with an acid.--

UNITED STATES PATENT AND TRADEMARK OFFICE
CERTIFICATE OF CORRECTION

PATENT NO. : 5,506,358
DATED : April 9, 1996
INVENTOR(S) : Akira Takase, et. al.

It is certified that error appears in the above-indentified patent and that said Letters Patent is hereby corrected as shown below:

Claim 20, column 25, line 16, change "denoted by -" to --denoted by --.

Signed and Sealed this

Thirtieth Day of July, 1996

Attest:

BRUCE LEHMAN

Attesting Officer     Commissioner of Patents and Trademarks